[11]    4,086,186
                                                                     [45]    Apr. 25, 1978

United States Patent [19]
Rubin et al.

[54] CRYSTALLINE ZEOLITE ZSM-34 AND METHOD OF PREPARING THE SAME

[75] Inventors: Mae K. Rubin, Bala Cynwyd, Pa.; Edward J. Rosinski, Pedricktown; Charles J. Plank, Woodbury, both of N.J.

[73] Assignee: Mobil Oil Corporation, New York, N.Y.

[21] Appl. No.: 738,771

[22] Filed: Nov. 4, 1976

[51] Int. Cl.$^2$ .................... C01B 33/28; B01J 29/06; B01J 29/28
[52] U.S. Cl. .................. 252/430; 252/431 R; 252/455 Z; 260/448 C; 423/328; 423/329
[58] Field of Search ............... 423/328, 329; 252/455 Z, 426, 438, 430, 431 R; 260/567.6 R, 567.6 M, 567.6 P, 448 C

[56] References Cited

U.S. PATENT DOCUMENTS

| | | | |
|---|---|---|---|
| 2,950,952 | 8/1960 | Breck | 423/329 |
| 4,021,447 | 5/1977 | Rubin et al. | 423/328 |

OTHER PUBLICATIONS

Aiello et al., "J. Chem. Soc. (A)" 1970, pp. 1470–1475.
Card et al., "Molecular Sieve Zeolites–I" ACS, 1971, pp. 230–236.
Robson et al., "Molecular Sieve Zeolites–II" ACS, 1971, pp. 417–425.
Breck, "Zeolite Molecular Sieves" 1974, pp. 633–645.

*Primary Examiner*—Edward J. Meros
*Attorney, Agent, or Firm*—Charles A. Huggett; Raymond W. Barclay

[57] ABSTRACT

A crystalline zeolite, designated ZSM-34, having the composition as synthesized and in anhydrous form, expressed as mole ratios of oxides as follows:

(0.5–1.3)$R_2O$: (0–0.15)$Na_2O$: (0.10–0.50)$K_2O$: $Al_2O_3$: $XSiO_2$ where R is the organic nitrogen-containing cation derived from choline [$(CH_3)_3NCH_2CH_2OH$] and X is 8 to 50, said zeolite having an X-ray diffraction pattern, identifying it as a member of the offretite-erionite family and the ability, after calcination at 1000° F for at least a period of time to remove the organic cation, to sorb at least 9.5 weight percent of n-hexane at ambient temperature and a n-hexane pressure of 20mm. Organic compound conversion is carried out in the presence of a catalytically-active form of said zeolite.

12 Claims, No Drawings

CRYSTALLINE ZEOLITE ZSM-34 AND METHOD OF PREPARING THE SAME

BACKGROUND OF THE INVENTION

1. Field of the Invention

This invention relates to novel crystalline aluminosilicates and to methods for their preparation. More particularly, this invention relates to novel crystalline aluminosilicates having unique sorption and catalytic properties, to methods for preparing the same and to organic compound conversion, especially hydrocarbon conversion, therewith.

2. Description of the Prior Art

Zeolitic materials, both natural and synthetic, have been demonstrated in the past to have catalytic capabilities for various types of organic compound conversion, especially hydrocarbon conversion. Certain of these zeolites comprise ordered porous crystalline aluminosilicates having a definite crystalline structure, as determined by X-ray diffraction, within which there are a large number of small cavities which may be interconnected by a series of still smaller channels or pores. Since the dimensions of these pores are such as to accept for adsorption molecules of certain dimensions while rejecting those of larger dimensions, these materials have come to be known as "molecular sieves" and are utilized in a variety of ways to take advantage of these properties.

These molecular sieves include a wide variety of positive ion-containing crystalline aluminosilicates, both natural and synthetic. Among the synthetic zeolites are those known as A, Y, L, D, R, S, T, Z, E, F, Q, B, X, erionite and offretite. All can be generally described as having a rigid 3-dimensional network of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is negatively charged and the composition is balanced by the inclusion in the crystal structure of a cation, for example, an alkali metal or an alkaline earth metal cation. Thus, a univalent positive sodium cation balances one negatively charged aluminosilicate tetrahedra. When an alkaline earth metal cation is employed in the crystal structure of an aluminosilicate, it balances two negatively charged aluminosilicate tetrahedra because of its doubly positive valence. The spaces between the tetrahedra are occupied by molecules of water prior to dehydration.

SUMMARY OF THE INVENTION

The present invention relates to a novel crystalline aluminosilicate zeolite hereinafter designated "Zeolite ZSM-34" or simply "ZSM-34", to a method for its preparation and to organic compound conversion and particularly hydrocarbon conversion therewith. ZSM-34 has the characteristic X-ray diffraction pattern set forth in Table 1, hereinbelow. ZSM-34 is identified by the composition, as synthesized and in anhydrous form, expressed in mole ratios of oxides, as follows:

$(0.5-1.3)R_2O$: $(0-0.15)Na_2O$: $(0.10-0.50)K_2O$: $Al_2O_3$: $XSiO_2$ where R is the organic nitrogen-containing cation derived from choline [$(CH_3)_3N\ CH_2CH_2OH$] and X is 8 to 50, preferably 8 to 30 and still more preferable 8 to 20.

ZSM-34 is similar in some respect to offretite or erionite but is distinguished from these zeolites in its capability, after calcination at 1000° F for at least a period of time sufficient to remove the organic cation, to sorb at least 9.5 weight percent of normal hexane, at ambient temperature and a n-hexane pressure of 20 mm., which is higher than that of any known member of the offretite-erionite family. ZSM-34 is further unique in that, as synthesized, it contains at least 0.5 mole of $R_2O$ per mole of $Al_2O_3$ in its structure, where R has the significance indicated hereinabove. ZSM-34 is further characterized by an apparent tabular morphology.

ZSM-34 has a crystalline structure where X-ray diffraction pattern shows the following characteristic lines:

TABLE 1

| °2θ | D(A) | Relative Intensity |
|---|---|---|
| 7.68 | 11.5 ± .2 | VS |
| 9.62 | 9.2 ;35 .2 | W |
| 11.67 | 7.58 ± .15 | M |
| 13.39 | 6.61 ± .13 | S |
| 14.01 | 6.32 ± .12 | W |
| 15.46 | 5.73 ± .11 | M |
| 16.57 | 5.35 ± .10 | W |
| 17.81 | 4.98 ± .10 | W |
| 19.42 | 4.57 ± .09 | S-VS |
| 20.56 | 4.32 ± .08 | VS |
| 21.36 | 4.16 ± .08 | W |
| 23.35 | 3.81 ± .07 | S-VS |
| 23.79 | 3.74 ± .07 | VS |
| 24.80 | 3.59 ± .07 | S-VS |
| 27.02 | 3.30 ± .06 | M-S |
| 28.33 | 3.15 ± .06 | M |
| 30.62 | 2.92 ± .05 | W |
| 31.41 | 2.85 ± .05 | VS |
| 31.93 | 2.80 ± .05 | W |
| 33.50 | 2.67 ± .05 | W |
| 35.68 | 2.52 ± .05 | W |
| 36.15 | 2.48 ± .05 | W-M |
| 38.30 | 2.35 ± .04 | W |
| 39.49 | 2.28 ± .04 | W |

These values were determined by standard techniques. The radiation was the K-alpha/doublet of copper and a scintillation counter spectrometer with a strip chart pen recorder was used. The peak heights, I, and the position as a function of 2 times theta, where theta is the Bragg angle were read from the spectrometer chart. From these, the relative intensities, $100I/I_o$, where $I_o$ is the intensity of the strongest line or peak and $d$ (obs.), the interplanar spacing in A, corresponding to the recording lines were calculated. The intensity in the table above is expressed as follows:

| Relative Intensity | 100 $I/I_o$ |
|---|---|
| VS (Very Strong) | 60 – 100 |
| S (Strong) | 40 – 60 |
| M (Medium) | 20 – 40 |
| W (Weak) | 0 – 20 |

ZSM-34 displays "1" odd lines not to be expected if it has the open offretite structure. These "1" odd lines (observed at about 9.6, 16.6, 21.4 and 31.9° 2θ) are broad in contrast to sharp ones in erionite. Without being limited by any theory, these data may be taken to indicate that ZSM-34 is not a physical mixture of offretite and erionite but rather an intergrowth of very small erionite domains throughout an offretite structure. These erionite domains appear as stacking faults and may contribute blockages to the main offretite channel.

Zeolite T has been reported by Bennett and Gard, Nature 214, 1005 (1967) to be a disordered intergrowth of erionite and offretite. Although the X-ray diffraction pattern of ZSM-34 indicates it to be an offretite with erionite intergrowth, ZSM-34 is unlike Zeolite T. As shown in Table 2 below ZSM-34 displays a line at 14.01° 2θ and the "1" odd lines at about 16.62 and 31.92° 2θ which are missing in Zeolite T. The latter zeolite, on the other hand, has some weak lines at about 14.74, 21.78, 24.28° 2θ as well as a doublet at about 31.2° 2θ.

A comparison of the X-ray diffraction pattern of ZSM-34 offretite, erionite and Zeolite T is shown below:

TABLE 2

| ZSM-34 | | Offretite[a] | | | |
|---|---|---|---|---|---|
| 2θ | I/I₀ | 2θ | ±Δθ | I/I₀ | min.–max. |
| 7.65 | 100 | 7.70 | .12 | 99 | 90–100 |
| 9.60 | broad 3 | — | — | — | |
| 11.65 | 25 | 11.75 | .08 | 39 | 0–85 |
| 13.37 | 52 | 13.38 | .15 | 67 | 29–100 |
| 14.01 | 10 | 14.06 | .07 | 31 | 0–55 |
| — | — | — | — | — | |
| 15.45 | 31 | 15.46 | .16 | 30 | 15–55 |
| 16.62 | broad 4 | — | — | — | |
| 17.82 | 10 | 17.77 | — | 10 | 0–10 |
| 19.40 | 64 | 19.49 | .11 | 42 | 0–85 |
| 20.50 | 61 | 20.50 | .17 | 69 | 43–90 |
| 21.35 | broad 7 | — | — | — | |
| — | — | 23.13 | .05 | 54 | 0–65 |
| 23.31 | 55 | 23.40 | .09 | 46 | 0–85 |
| 23.67 | 86 | 23.75 | .18 | 83 | 0–100 |
| — | — | — | — | — | |
| 24.77 | 86 | 24.88 | .15 | 62 | 3–100 |
| — | — | 26.24 | .26 | 5 | 0–10 |
| 27.03 | 34 | 26.98 | .27 | 36 | 19–55 |
| — | — | 27.31 | .10 | 18 | 0–55 |
| — | — | 28.16 | .29 | 18 | 5–55 |
| 28.25 | 40 | 28.44 | .07 | 47 | 0–60 |
| — | — | — | — | — | |
| 30.55 | 9 | 30.58 | .20 | 11 | 0–25 |
| — | — | 31.00 | .05 | 68 | 0–71 |
| 31.35 | 84 | 31.31 | .14 | 44 | 12–80 |
| — | — | 31.57 | .07 | 73 | 0–85 |
| 31.92 | — | — | — | — | |
| 33.45 | 16 | 33.48 | .34 | 23 | 3–55 |
| — | — | — | — | — | |
| 35.70 | 4 | 35.79 | .19 | 14 | 5–31 |
| 36.10 | 21 | 36.06 | .06 | 8 | 0–10 |
| — | — | 36.29 | .08 | 25 | 0–55 |

| Erionite[b] | | | | Linde T | |
|---|---|---|---|---|---|
| 2θ | ±Δθ | I/I₀ | min.–max. | 2θ | I/I₀ |
| 7.72 | .10 | 83 | 5–100 | 7.72 | 100 |
| 9.69 | .14 | 38 | 0–100 | 9.63 | 4 |
| 11.73 | .34 | 25 | 3–85 | 11.74 | 13 |
| 13.41 | .17 | 69 | 38–100 | 13.35 | 54 |
| 14.02 | .14 | 19 | 0–55 | — | — |
| — | — | — | — | 14.74 | 2 |
| 15.49 | .13 | 22 | 0–55 | 15.44 | 6 |
| 16.57 | .12 | 21 | 7–55 | — | — |
| 17.79 | .16 | 12 | 0–25 | 17.78 | 2 |
| 19.46 | .22 | 29 | 0–85 | 19.43 | 8 |
| 20.54 | .16 | 60 | 0–90 | 20.46 | 45 |
| 21.37 | .17 | 34 | 10–85 | 21.35 | 3 |
| — | — | — | — | 21.78 | 2 |
| 23.35 | .13 | 48 | 14–90 | 23.27 | 16 |
| 23.75 | .21 | 64 | 0–100 | 23.64 | 56 |
| 24.36 | .23 | 20 | 0–45 | 24.28 | 1 |
| 24.87 | .07 | 47 | 0–100 | 24.80 | 30 |
| 26.24 | .13 | 9 | 1–25 | 26.04 | 2 |
| 26.99 | .14 | 32 | 17–55 | 26.92 | 16 |
| 27.26 | .27 | 25 | 0–55 | — | — |
| 28.15 | .11 | 18 | 0–38 | 28.04 | 12 |
| 28.36 | .06 | 34 | 0–55 | 28.29 | 18 |
| 28.79 | .20 | 10 | 0–25 | — | — |
| 30.54 | .28 | 17 | 0–55 | 30.47 | 11 |
| — | — | — | — | 31.15 | 38 |
| 31.26 | .10 | 41 | 0–75 | 31.38 | 45 |
| 31.54 | .13 | 61 | 0–100 | — | — |
| 31.92 | .15 | 39 | 0–85 | — | — |
| 33.54 | .20 | 28 | 0–85 | 33.41 | 11 |
| 34.71 | .17 | 15 | 0–25 | 34.32 | 2 |
| 35.80 | .06 | 18 | 0–30 | 35.83 | 8 |
| 35.98 | .06 | 30 | 0–70 | 36.09 | 13 |
| 36.22 | .07 | 24 | 0–55 | — | — |

[a]Average of eight offretites in the literature
[b]Average of eleven erionites in the literature The equilibrium adsorption characteristics of ZSM-34 are compared to members of the offretite-erionite family in Table 3 below.

TABLE 3

| Sample | H₂O Wt. % | H₂O cc/g | n-Hexane Wt. % | n-Hexane cc/g | Cyclohexane Wt. % | Cyclohexane cc/g |
|---|---|---|---|---|---|---|
| ZSM-34 | 20.1 | 0.20 | 10.7 | 0.16 | 4.3 | 0.06 |
| Synthetic Offretite | 16.5 | 0.16 | 8.8 | 0.13 | 7.8 | 0.10 |
| | 14.8 | 0.15 | 7.9 | 0.12 | 2.9 | 0.04 |
| Synthetic Erionite | 18.0 | 0.18 | 6.5 | 0.10 | 1.0 | 0.01 |
| Natural Erionite | 15.6 | 0.16 | 5.3 | 0.08 | 0.9 | 0.01 |
| Zeolite T | 18.2 | 0.18 | (6.6 | 0.11)* | 0.8 | 0.01 |

*Values in brackets are for n-pentane.

The above adsorption data were determined as follows: A weighed sample of the zeolite was contacted with the desired pure adsorbate vapor in the adsorption chamber at a pressure less than the vapor - liquid equilibrium pressure of the adsorbate at ambient temperature, e.g. about 25° C. This pressure was kept constant during the adsorption period which did not exceed about 8 hours. Adsorption was complete when a constant pressure in the adsorption chamber was reached, i.e., 12 mm. of mercury for water and 20 mm. for n-hexane and cyclohexane. The increase in weight was calculated as the adsorption capacity of the sample.

It will be evident from the above tabulated data that ZSM-34 was characterized by the highest sorptive capacity for water and n-hexane. It is a unique property of ZSM-34 that this zeolite, in contrast to other known members of the offretite-erionite family, has the capability of sorbing at least 9.5 weight percent of n-hexane.

The original cations of ZSM-34 can be replaced in accordance with techniques well-known in the art, at least in part, by ion exchange with other cations preferably after calcination. Preferred replacing cations include tetraalkylammonium cations, metal ions, ammonium ions, hydrogen ions, and mixtures of the same. Particularly preferred cations are those which render the zeolite catalytically active, especially for hydrocarbon conversion. These include hydrogen, rare earth metals, aluminum, manganese, and metals of Groups II and VIII of the Periodic Table.

ZSM-34 can be suitably synthesized by preparing a gel reaction mixture having a composition, in terms of mole ratios of oxides, falling within the following ranges:

| | Broad | Preferred |
|---|---|---|
| $SiO_2/Al_2O_3$ | 10–70 | 10–55 |
| $OH^-/SiO_2$ | 0.3–1.0 | 0.3–0.8 |
| $H_2O/OH^-$ | 20–100 | 20–80 |
| $K_2O/M_2O$ | 0.1–1.0 | 0.1–1.0 |
| $R^+/R^+ + M^+$ | 0.1–0.8 | 0.1–0.50 | where $R^+$ is choline [$(CH_3)_3$-N-$CH_2CH_2OH$] and M is Na + K and maintaining the mixture until crystals of the zeolite are formed. $OH^-$ is calculated from inorganic base not neutralized by any added mineral acid or acid salt. Resulting zeolite crystals are separated and recovered. Typical reaction conditions consist of heating the foregoing reaction mixture to a temperature of from about 80° to about 175° C for a period of time of from about 12 hours to 200 days. A more preferred temperature range is from about 90° to 160° C. with the amount of time at a temperature in such range being from about 12 hours to 50 days.

The resulting crystalline product is separated from the mother liquor by filtration, water washing and drying, e.g., at 230° F for from 4 to 48 hours. Milder conditions may be employed, if desired, e.g., room temperature under vacuum.

ZSM-34, when employed either as an adsorbent or as a catalyst in a hydrocarbon conversion process should be at least partially dehydrated and the organic cation at least partially removed. This can be done by heating to a temperature in the range of 200° to 750° C in an atmosphere, such as air, nitrogen, etc., and at atmospheric or subatmospheric pressure for between 1 and 48 hours. Dehydration can also be preformed at lower temperatures merely by placing the catalyst in a vacuum, but a longer time is required to obtain a sufficient amount of dehydration.

The composition of ZSM-34 can be prepared utilizing materials which supply the appropriate oxide. Such compositions include, for example, sodium aluminate, alumina, sodium silicate, silica hydrosol, silica gel, silicic acid, sodium hydroxide, aluminum sulfate, potassium hydroxide, potassium silicate, and a choline compound such as the halide, i.e. fluoride, chloride or bromide; sulfate, acetate; or nitrate. It will be understood that each oxide component utilized in the reaction mixture for preparing ZSM-34 can be supplied by one or more initial reactants and they can be mixed together in any order. The reaction mixture can be prepared either batchwise or continuously. Crystal size and crystallization time of the ZSM-34 composition will vary with the nature of the reaction mixture employed.

In many instances, it is desired to incorporate the ZSM-34 with another material resistant to the temperature and other conditions employed in organic conversion processes. Such materials include active and inactive materials and synthetic or naturally occurring zeolites as well as inorganic materials such as clays, silica, and/or metal oxides. The latter may be either naturally occurring or in the form of gelatinous precipitates or gels including mixtures of silica and metal oxides. Use of a material in conjunction with ZSM-34, i.e., combined therewith which is active, tends to improve the conversion and/or selectively of the catalyst in certain organic conversion processes. Inactive materials suitably serve as diluents to control the amount of conversion in a given process so that products can be obtained economically and in orderly manner without employing other means for controlling the rate of reaction. Normally, zeolitic materials have been incorporated into naturally occurring clays, e.g. bentonite and kaolin, to improve the crush strength of the catalyst under commercial operating conditions. These materials, i.e., clays, oxides and the like function as binders for the catalyst. It is desirable to provide a catalyst having good crush strength, because in a petroleum refinery the catalyst is often subjected to rough handling which tends to break the catalyst down into powder-like materials which cause problems in processing. These clay binders have been employed for the purpose of improving the crush strength of the catalyst.

Naturally occurring clays which can be composited with the ZSM-34 catalyst include the montmorillonite and kaolin family, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the above materials, ZSM-34 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, and silica-magnesia-zirconia. The matrix can be in the form of a cogel. The relative proportion of finely divided ZSM-34 and inorganic oxide gel matrix may vary widely with the crystalline aluminosilicate content ranging from about 1 to about 90 percent by weight and more usually in the range of about 2 to about 50 percent by weight of the composition.

As noted hereinabove, ZSM-34 is useful as a catalyst in organic compound conversion and particularly hydrocarbon conversion. Representative of such processes are cracking;hydrocarcking; alkylation; isomerization of n-paraffin and naphthenes; polymerization of compounds containing an olefinic or acetylenic carbon-to-carbon linkage such as propylene, isobutylene and butene-1; reforming, isomerization of polyalkyl substituted aromatics, e.g., ortho xylene and disproportionation of aromatics, such as toluene to provide a mixture of benzene, xylenes, and higher methylbenzenes. The ZSM-34 catalysts are characterized by high selectivity, under the conditions of hydrocarbon conversion, to provide a high percentage of desired products.

ZSM-34 is generally used in the ammonium, hydrogen or other univalent or multivalent cationic form. It can also be used in intimate combination with a hydrogenation component such as tungsten, vanadium, molybdenum, rhenium, nickel, cobalt, chromium, manganese or a noble metal, such as platinum or palladium when a hydrogenation-dehydrogenation function is to be performed. Such component may be exchanged into the zeolite, impregnated thereon or physically intimately admixed therewith.

Employing the ZSM-34 catalyst of the invention for cracking, hydrocarbon charge stocks can be cracked at a liquid hourly space velocity between about 0.5 and 50, a temperature between 550° and 1100° F, a pressure between about atmospheric and several hundred atmospheres. When used for polymerization of olefins, the temperature is generally between about 550° and about 850° F, utilizing a weight hourly space velocity between about 0.1 and about 30 and a pressure between about 0.1 and about 50 atmospheres.

The following examples will serve to illustrate synthesis of the new crystalline aluminosilicate described hereinabove.

EXAMPLE 1

4.43 grams of KOH (86.4%), 13 grams of NaOH (96%) and 5.74 grams of sodium aluminate (43.1% Al$_2$O$_3$, 33.1% Na$_2$O, 24% H$_2$O) were dissolved in 90 grams of water. Choline chloride (38 grams) was added to the resulting solution, followed by the addition of 130 grams of colloidal silica (30 Wt.% SiO$_2$ and 70 Wt.% H$_2$O). A gel formed having the following molar composition:

$$\frac{SiO_2}{Al_2O_3} = 26.6$$

$$\frac{R^+}{R^+ + M^+} = 0.38$$

-continued $$\frac{OH^-}{SiO_2} = 0.68$$

$$\frac{H_2O}{OH^-} = 22.9$$

$$\frac{K_2O}{M_2O} = 0.15$$

where R is choline [$(CH_3)_3NCH_2CH_2OH$] and M is Na + K.

The resulting gel was mixed for 15 minutes and allowed to crystallize in a polypropylene container at 210° F for 25 days. The crystalline product obtained was separated from the mother liquor by filtration, water washed and dried at 230° F. This product, upon analysis, was found to have the following composition molar ratio:

0.64 $R_2O$: 0.47$K_2O$: 0.13 $Na_2O$: $Al_2O_3$: 10.8 $SiO_2$ and the following X-ray diffraction pattern:

| °2θ | D(A) | INTENSITY |
|---|---|---|
| 7.65 | 11.56 | 100 |
| 9.60 | 9.21 | 3 |
| 11.65 | 7.60 | 25 |
| 13.37 | 6.62 | 52 |
| 14.01 | 6.32 | 10 |
| 15.45 | 5.74 | 31 |
| 16.62 | 5.33 | 4 |
| 17.82 | 4.98 | 10 |
| 19.40 | 4.58 | 64 |
| 20.50 | 4.33 | 61 |
| 21.35 | 4.16 | 7 |
| 23.31 | 3.82 | 55 |
| 23.67 | 3.76 | 86 |
| 24.77 | 3.59 | 86 |
| 27.03 | 3.30 | 34 |
| 28.25 | 3.16 | 40 |
| 30.55 | 2.926 | 9 |
| 31.35 | 2.853 | 84 |
| 31.92 | 2.804 | 11 |
| 33.45 | 2.679 | 16 |
| 35.70 | 2.515 | 4 |
| 36.10 | 2.488 | 21 |
| 39.41 | 2.286 | 4 |
| 41.02 | 2.200 | 7 |
| 42.90 | 2.108 | 6 |
| 43.50 | 2.080 | 4 |
| 45.75 | 1.983 | 4 |
| 46.42 | 1.956 | 3 |
| 48.15 | 1.890 | 19 |
| 48.83 | 1.865 | 5 |
| 49.84 | 1.830 | 6 |

A portion of the product of Example 1, calcined at 1000° F for 16 hours, had the following sorption and surface area properties:

| Sorption | | Wt. % |
|---|---|---|
| Cyclohexane | = | 4.4 |
| n-Hexane | = | 11.5 |
| Water | = | 22.2 |
| Surface area $m^2/g$ | = | 523 |

EXAMPLES 2 - 7

These examples were carried out in a manner similar to that of Example 1 and had substantially the same x-ray diffraction pattern. The composition of the gel obtained and the product composition, together with adsorption properties and surface area are shown below in Table 4.

TABLE 4

| EXAMPLE | 2 | 3 | 4 | 5 | 6 | 7 |
|---|---|---|---|---|---|---|
| Gel Molar Ratio | | | | | | |
| $SiO_2/Al_2O_3$ | 13.4 | 13.4 | 26.8 | 26.8 | 26.8 | 26.8 |
| $R+^{(1)}/R^+ + M^{+(2)}$ | 0.47 | 0.47 | 0.47 | 0.31 | 0.50 | 0.47 |
| $CH^-/SiO_2$ | 0.48 | 0.47 | 0.48 | 0.48 | 0.42 | 0.48 |
| $H_2O/OH^-$ | 32.2 | 32.8 | 32.5 | 32.5 | 37.0 | 32.5 |
| $K_2O/M_2O$ | 0.22 | 0.22 | 0.22 | 0.22 | 0.11 | 0.22 |
| Crystallization | | | | | | |
| Days at 210° F | 35 | 32 | 25 | 135 | 196 | 48 |
| X-Ray Analysis | ZSM-34 | ZSM-34 | ZSM-34 | ZSM-34[3] | ZSM-34[3] | ZSM-34 |
| Product Composition (Molar Ratio) | | | | | | |
| $Al_2O_3$ | 1.0 | 1.0 | 1.0 | 1.0 | 1.0 | 1.0 |
| $SiO_2$ | 9.8 | 10.2 | 13.3 | 15.0 | 17.8 | 13.9 |
| $Na_2O$ | 0.14 | 0.07 | 0.12 | 0.12 | 0.16 | 0.02 |
| $K_2O$ | 0.40 | 0.36 | 0.27 | 0.21 | 0.11 | 0.22 |
| $R_2O$ | 0.66 | 0.67 | 0.57 | 1.02 | 1.21 | 0.94 |
| Adsorption, wt % (calcined 16 hrs at 1000° F) | | | | | | |
| Cy-$C_6$ | 4.3 | 4.9 | 5.2 | 5.2 | 4.4 | 6.4 |
| N-$C_6$ | 10.7 | 10.3 | 11.2 | 11.3 | 10.3 | 11.3 |
| $H_2O$ | 20.1 | 20.9 | 19.0 | 18.9 | 16.2 | 15.9 |
| Surface Area, $m^2/g$ | 532 | 524 | 521 | 536 | 502 | 520 |

[1]$R+ = [(CH_3)_3N-CH_2CH_2OH]^+$
[2]$M+ = Na^+ + K^+$
[3]Possibly contains some Levynite.

EXAMPLE 8

ZSM-34 can also be synthesized from mixtures containing aluminum sulfate and sodium silicate. Utilizing these reactants, a solution containing 15.98 grams of $Al_2(SO_4)_3 \cdot 18 H_2O$ in 100 grams of water was added to a solution of 135.4 grams of Q-Brand sodium silicate (22.8% $SiO_2$, 8.9% $Na_2O$ and 62% $H_2O$) and 40 grams of water to which 4.4 grams of KOH (86.4%) and 38 grams of choline chloride had been added. A gel formed having the following molar composition:

$$\frac{SiO_2}{Al_2O_3} = 27.2$$

$$\frac{R^+}{R^+ + M^+} = 0.46$$

$$\frac{OH^-}{SiO_2} = 0.48$$

$$\frac{H_2O}{OH^-} = 39.6$$

$$\frac{K_2O}{M_2O} = 0.22$$

This material was permitted to crystallize in a propylene container by exposure to a temperature of 210° F.

for 98 days. The crystalline product obtained was filtered, water washed and dried at 230° F. and upon analysis was found to be ZSM-34 having the following molar composition:

0.93 R$_2$O: 0.22 K$_2$O: 0.08 Na$_2$O: Al$_2$O$_3$: 13.7 SiO$_2$

The product obtained, after calcination at 1000° F for 16 hours, had the following sorptive and surface area properties:

| Sorption | Wt. % |
|---|---|
| Cyclohexane | 3.1 |
| n-Hexane | 10.5 |
| Water | 19.0 |
| Surface Area M$^2$/g | 528 |

EXAMPLE 9

ZSM-34 can also be synthesized from potassium silicate. Utilizing this reactant, a solution of aluminum sulfate containing 15.98 grams of Al$_2$(SO$_4$)$_3$. 18 H$_2$O and 4.4 grams of H$_2$SO$_4$ in 100 grams of water was added to a solution of 187.5 grams of potassium silicate (20.8% SiO$_2$, 8.3%K$_2$O and 72.9% H$_2$), 0.2 gram of quercetin and 20 grams of water. Thereafter, 9.6 grams of NaOH and 38 grams of choline chloride were added.

A gel formed having the following composition:

$$\frac{SiO}{Al_2O_3} = 27.2$$

$$\frac{R^+}{R^+ + M^+} = 0.44$$

$$\frac{OH^-}{SiO_2} = 0.52$$

$$\frac{H_2O}{OH^-} = 40.4$$

$$\frac{K_2O}{M_2O} = 0.97$$

This gel, after mixing for 15 minutes, was heated at 210° F for 73 days. After filtration, the product was water washed and dried at 230° C. Upon analysis, the product was found to be ZSM-34 having the following molar composition:

0.94 R$_2$O: 0.4 K$_2$O: 0.02 Na$_2$O: Al$_2$O$_3$: 14.5 SiO$_2$

After calcination, this product had the following sorptive and surface area properties:

| Sorption | | Wt.% |
|---|---|---|
| Cyclohexane | = | 5.3 |
| n-Hexane | = | 10.7 |
| Water | = | 17.8 |
| Surface Area m$^2$/g | = | 499 |

EXAMPLE 10

ZSM-34 was prepared by mixing together the following solutions:

A. Caustic Aluminate 69.89 grams sodium aluminate (20% Na, 43.1% Al$_2$O$_3$ and balance H$_2$O)
29.28 grams NaOH (77.5 wt. % Na$_2$O)
26.4 grams KOH (86.4% KOH)
540 grams H$_2$O B. Silica Solution 780 grams Colloidal silica sol. (30% SiO$_2$).

C. Choline Chloride 228 grams

Solution C was added to Solution A in a 2 liter autoclave with mixing and then Solution B was added, followed by a 15 minute continuous mixing. The autoclave was then sealed and heated to and held at 300° F for 8 days. The contents were stirred continuously during the 8 days crystallization period.

The autoclave and its contents were then cooled to room temperature, filtered and washed to separate the crystalline product from the reaction mixture.

On analysis, the resulting product was established by X-ray diffraction pattern to be ZSM-34 containing:

| | Wt. % |
|---|---|
| Na | 0.68 |
| K | 3.59 |
| Al$_2$O$_3$ | 13.5 |
| SiO$_2$ | 78.5 |
| N | 2.0 |

This product had the following molar composition:
0.54 R$_2$O: 0.11 Na$_2$O: 0.35 K$_2$O: Al$_2$O$_3$: 9.87 SiO$_2$.

Adsorption and surface area properties were as follows:

| Sorption | | Wt. %, |
|---|---|---|
| Cyclohexane | = | 3.5 |
| n-Hexane | = | 9.6 |
| Water | = | 19.7 |
| Surface Area m$^2$/g | | 448 |

EXAMPLE 11

This example was carried out in the same manner as that of Example 10 except the reaction temperature was reduced to 250° F and the reaction time extended to 11 days.

The resulting product had the following molar composition:

0.52 R$_2$O: 0.159 Na$_2$O: 0.34 K$_2$O: Al$_2$O$_3$: 9.65 SiO$_2$ and a surface area of 512 m$^2$/gram.

EXAMPLE 12

A sample of ZSM-34, prepared as in Example 7, was ion exchanged by treatment with a 10 weight percent aqueous solution of ammonium chloride by contacting 5 times for 1 hour each contact at 185° F and thereafter calcining in air for 10 hours at 1000° F to yield the hydrogen form of the zeolite.

Catalytic cracking of n-hexane was carried out using the resulting exchanged ZSM-34 as catalyst, by means of an alpha test which is described in the Journal of Catalysis Vol IV, No. 4, August 1965, pages 527–529.

In the test 0.5cc of catalyst sized 14 to 25 mesh was contacted with n-hexane at a vapor pressure of 110 mm. The test was run at 700° F with products analyzed after 5 minutes of run giving 21.3 wt. % conversion. The calculated α value or relative activity for cracking n-hexane compared to standard silica-alumina was 877.

EXAMPLE 13

Cracking with NH$_4$+ exchanged ZSM-34 prepared as in Example 6 was evaluated as described under Example 12 but at 800° F giving 22.1 wt. % conversion after 5 minutes which calculates to an α value of 163.

EXAMPLE 14

Propylene polymerization with the hydrogen form of ZSM-34 prepared as in Example 6 was run as described below.

Propylene was passed over a calcined 2.6cc (1.0348 g) sample of ZSM-34 catalyst contained in a tubular glass reactor equipped with an axial thermowell at atmospheric pressure. The catalyst was preheated in air flowing at 10cc/minute at 1000° F for 1.25 hour and then purged with helium, while the reactor temperature lined out at 600° F.

The reactor effluent was collected between the 1 and 2 hours on stream and was analyzed. At these conditions of 1.3 WHSV, 600° F, 81.7 wt. % of the propylene was converted based on recovered products. On the basis of converted products, the yield was 96.6 wt. % C$_4$+ and 83.7 wt. % C$_5$+.

Evaluating the same catalyst at 7.9 WHSV and 600° F gave a 34.2 wt. % conversion of the propylene with a yield based on converted products of 97.5 wt. % C$_4$+ and 90.6 wt. % C$_5$+. At a 8.4 WHSV and 700° F the conversion was 52 wt. % with a yield of 82.5 wt. % C$_5$+ based on converted products.

EXAMPLE 15

Cracking with a calcined NH$_4$+ exchanged ZSM-34 prepared as in Example 5 was evaluated as described under Example 12 but at 800° F giving 27 wt % conversion after 5 minutes which calculates to an α value of 205.

EXAMPLE 16

Propylene polymerization with the hydrogen form ZSM-34, prepared as in Example 15, was evaluated as described under Example 14. Here 0.67cc (0.25g) catalyst at 600° F was contacted with the propylene. At these conditions 7.9 WHSV, 600° F, 31.6 wt. % was converted and on the basis of converted products the yield was 96.8 wt. % C$_4$+ and 88.1 wt. % C$_5$+. Another run employing 2.5 cc (1.0249 g) catalyst at 600° F at these conditions of 1.3 WHSV, 76.1 wt. % of the propylene charge was converted to yield 96 wt. % C$_4$+ and 83 wt. % C$_5$+ based on converted products.

EXAMPLE 17

Cracking with NH$_4$+ exchanged ZSM-34 prepared as in Example 3 was evaluated as described under Example 12 at 800° F. The conversion was 38.9 after 5 minutes which calculates to an α value of 322.

EXAMPLE 18

Propylene polymerization with the hydrogen form of ZSM-34, prepared as in Example 17 was evaluated as described under Example 14.

In evaluating this example 0.6cc (0.2535 g) was used and evaluated at 600° F at these conditions of 7.7 WHSV and 600° F 40.1 wt. % of the propylene, on recovered basis, was converted yielding 97.1 wt. % C$_4$+ and 86.8 wt. % C$_5$+ based on converted products.

It is to be understood that the foregoing description is merely illustrative of preferred embodiments of the invention of which many variations may be made by those skilled in the art within the scope of the following claims without departing from the spirit thereof.

What is claimed is:

1. A crystalline aluminosilicate zeolite having a composition, as synthesized and in anhydrous form, in terms of mole ratios of oxides as follows:

(0.5–1.3)R$_2$O: (0–0.15 Na$_2$O) : (0.10–0.50) K$_2$O : Al$_2$O$_3$ : X SiO$_2$ where R is the organic nitrogen-containing cation derived from choline and X is 8 to 50, said zeolite being characterized by:

(1) an X-ray powder diffraction pattern set forth in Table 1 of the specification; and
(2) the capability, after calcination at 1000° F for at least a time to remove the organic cation, of sorbing at least 9.5 weight percent of n-hexane at ambient temperature and a n-hexane pressure of 20 mm.

2. A crystalline aluminosilicate zeolite resulting from thermal treatment of the composition of claim 1 at a temperature of from about 200° C to about 750° C.

3. The composition of claim 1 wherein X is 8 to 30.

4. The composition of claim 1 wherein X is 8 to 20.

5. The crystalline aluminosilicate zeolite of claim 1 which has undergone ion exchange with ammonium, hydrogen, rare earth metal, aluminum, manganese or metals of Groups II or VIII of the Periodic Table.

6. The crystalline aluminosilicate zeolite of claim 5 wherein the replacing cation is hydrogen or ammonium.

7. The crystalline aluminosilicate zeolite of claim 2 which has undergone ion exchange with ammonium, hydrogen, rare earth metal, aluminum, manganese or metals of Groups II or VIII of the Periodic Table.

8. The crystalline aluminosilicate of claim 7 wherein the replacing cation is hydrogen or ammonium.

9. A method of preparing a crystalline aluminosilicate zeolite as defined in claim 1 which comprises preparing a mixture containing sodium oxide, potassium oxide, silica, alumina, a choline compound and water and having a composition in terms of mole ratios of oxides, falling within the following ranges:

SiO$_2$/Al$_2$O$_3$ — 10–70
OH$^-$/SiO$_2$ — .3–1.0
H$_2$O/OH$^-$ — 20–100
K$_2$O/M$_2$O — 0.1–1.0
R$^+$/R$^+$ + M$^+$ — 0.1–0.8 where R$^+$ is choline and M is sodium + potassium; maintaining the mixture at a temperature of between about 80° and about 175° C until the crystals of said aluminosilicate zeolite are formed and separating and recovering said crystals.

10. A method of preparing a crystalline aluminosilicate zeolite according to claim 9 wherein said mixture has a composition falling within the following ranges:

SiO$_2$/Al$_2$O$_3$ — 10–55
OH$^-$/SiO$_2$ — 0.3–0.8
H$_2$O/OH$^-$ — 20–80
K$_2$O/M$_2$O — 0.1–1.0
R$^+$/R$^+$ + M$^+$ — 0.1–0.50

11. The crystalline aluminosilicate zeolite of claim 1 admixed with a binder therefor.

12. The crystalline aluminosilicate zeolite composition of claim 11 wherein said binder is an inorganic oxide.

* * * * *

UNITED STATES PATENT AND TRADEMARK OFFICE
CERTIFICATE OF CORRECTION

PATENT NO. : 4,086,186
DATED : April 25, 1978
INVENTOR(S) : MAE K. RUBIN, EDWARD J. ROSINSKI and CHARLES J. PLANK It is certified that error appears in the above–identified patent and that said Letters Patent are hereby corrected as shown below:

Column 2, line 18   "9.2 ;35.2 should be --9.2 + .2 --.
Column 3, line 34   Table 2, line 34 (ZSM-34, I/Io column) insert --11--.
Column 8, line 26   Table 4 "CH$^-$/SiO$_2$" should be --OH$^-$/SiO$_2$--.
Column 8, line 55   "$\frac{SiO_2}{Al_3O_3}$" should be --$\frac{SiO_2}{Al_2O_3}$--.
Column 10, line 38   "m$^2$1g" should be --m$^2$/g--.

*Signed and Sealed this*

*Third* Day of *October 1978*

[SEAL]

Attest:

RUTH C. MASON
*Attesting Officer*

DONALD W. BANNER
*Commissioner of Patents and Trademarks*